(12) United States Patent
Tkaczyk et al.

(10) Patent No.: US 8,575,558 B2
(45) Date of Patent: Nov. 5, 2013

(54) DETECTOR ARRAY WITH A THROUGH-VIA INTERPOSER

(75) Inventors: John Eric Tkaczyk, Delanson, NY (US); James Wilson Rose, Guilderland, NY (US); Jonathan David Short, Saratoga Springs, NY (US); Charles Gerard Woychik, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 12/956,139

(22) Filed: Nov. 30, 2010

(65) Prior Publication Data

US 2012/0133054 A1    May 31, 2012

(51) Int. Cl.
    *G01T 1/24*    (2006.01)
(52) U.S. Cl.
    USPC ..................................... 250/370.09
(58) Field of Classification Search
    USPC .............. 250/370.09; 257/E23.011; 378/19
    See application file for complete search history.

(56) References Cited

U.S. PATENT DOCUMENTS

| | | | |
|---|---|---|---|
| 5,757,878 A * | 5/1998 | Dobbs et al. .................... | 378/19 |
| 6,303,992 B1 | 10/2001 | Van Pham et al. | |
| 6,403,964 B1 * | 6/2002 | Kyyhkynen ............ | 250/370.09 |
| 6,618,267 B1 | 9/2003 | Dalal et al. | |

(Continued)

FOREIGN PATENT DOCUMENTS

| | | |
|---|---|---|
| EP | 1598863 A1 | 11/2005 |
| JP | 2005051155 A * | 2/2005 |

(Continued)

OTHER PUBLICATIONS

Beelen-Hendrikx C et al.; "Trends in electronic packaging and assembly for portable consumer products"; Date of Current Version: Aug. 6, 2002; INSPEC Accession No. 6887122; Print ISBN: 0-7803-6644-1; Abstract 1 page, <doi:10.1109/EPTC.2000.906345>.

(Continued)

*Primary Examiner* — Constantine Hannaher
(74) *Attorney, Agent, or Firm* — Scott J. Asmus

(57) ABSTRACT

A method for forming a sensor stack is presented. The method includes providing a substrate having a first side and a second side. Furthermore, the method includes disposing an integrated circuit having a first side and a second side on the first side of the substrate, where the integrated circuit comprises a first plurality of contact pads disposed on the first side of the integrated circuit. The method also includes providing a sensor array having a plurality of sensor elements, wherein each of the sensor elements has a first side and a second side, and wherein the sensor array comprises a second plurality of contact pads disposed on the second side of the sensor array. Furthermore, the method includes disposing an interposer having one or more interposer elements and one or more through vias disposed therethrough between the one or more sensor elements of the sensor array and the integrated circuit to raise the sensor array away from the first side of the integrated circuit such that a plane of the one or more sensor elements is locally normal to a sensor stack normal, wherein the interposer is configured to operationally couple the second side of the sensor elements in the sensor array to the first side of the integrated circuit. In addition, the method includes operationally coupling the first plurality of contact pads on the first side of the integrated circuit to a second plurality of contact pads on the second side of the sensor array to form a tileable sensor stack.

27 Claims, 9 Drawing Sheets

(56) References Cited

U.S. PATENT DOCUMENTS

| | | |
|---|---|---|
| 6,984,886 B2 | 1/2006 | Ahn et al. |
| 7,282,382 B2 | 10/2007 | Rieve et al. |
| 7,289,336 B2 | 10/2007 | Burdick, Jr. et al. |
| 7,361,593 B2 | 4/2008 | Freeman et al. |
| 7,423,335 B2 | 9/2008 | Yang et al. |
| 2003/0155516 A1 | 8/2003 | Spartiotis et al. |
| 2008/0068815 A1 | 3/2008 | Astley et al. |
| 2008/0165921 A1 | 7/2008 | Tkaczyk et al. |
| 2009/0085225 A1* | 4/2009 | Park .................... 257/777 |
| 2010/0156243 A1* | 6/2010 | Weekamp et al. ........... 310/334 |
| 2012/0007236 A1* | 1/2012 | Bae ....................... 257/737 |

FOREIGN PATENT DOCUMENTS

| | | |
|---|---|---|
| WO | 0065376 A1 | 11/2000 |
| WO | 2004038810 A2 | 5/2004 |
| WO | 2005047859 A2 | 5/2005 |
| WO | 2008012748 A2 | 1/2008 |
| WO | 2008038183 A1 | 4/2008 |

OTHER PUBLICATIONS

Tkaczyk et al., "Tileable Sensor Array", U.S. Appl. No. 12/956,194, filed Nov. 30, 2010.

Heanue, Joseph A. et al, "CdZnTe detector array for a scanning-beam digital x-ray system", Proc. SPIE 3659, Medical Imaging 1999: Physics of Medical Imaging, 718, May 28, 1999.

Search Report from corresponding NL Application No. 2007885 dated Jun. 13, 2013.

* cited by examiner

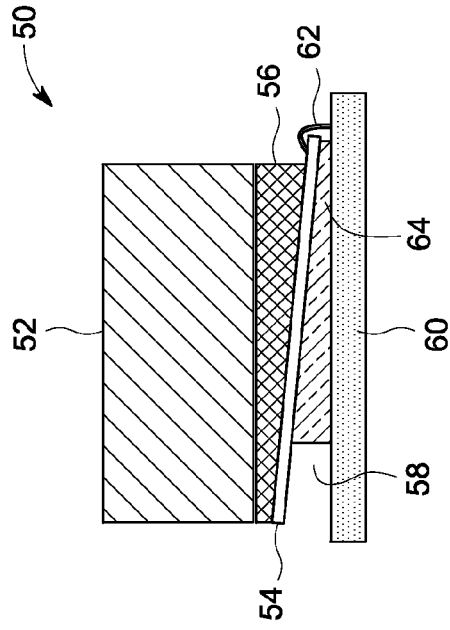
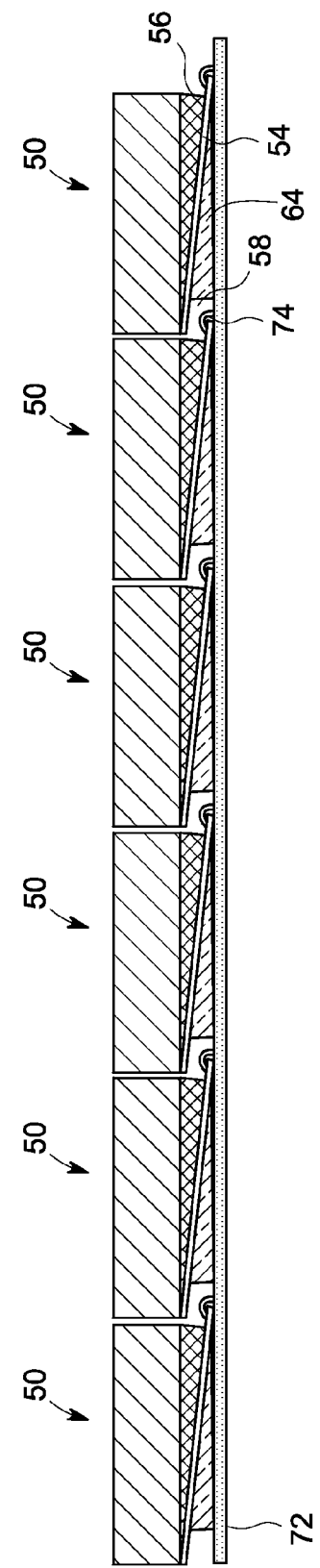

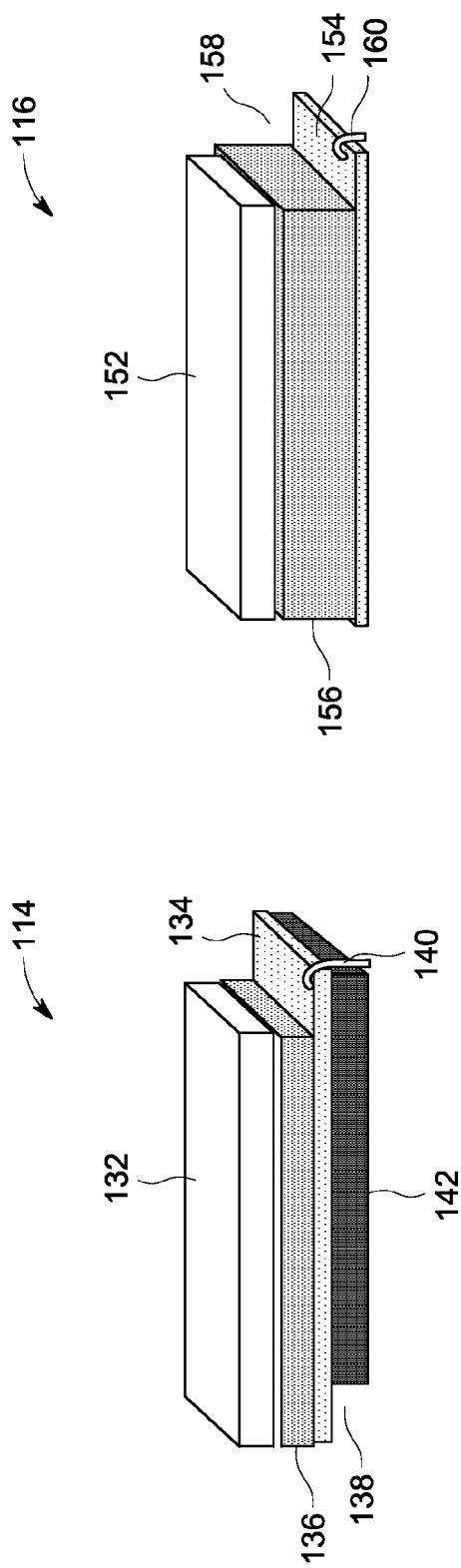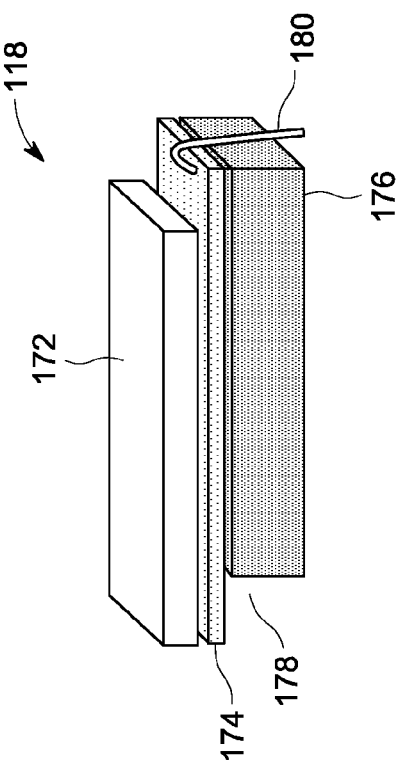
FIG. 9
FIG. 10
FIG. 11

DETECTOR ARRAY WITH A THROUGH-VIA INTERPOSER

BACKGROUND

Embodiments of the present disclosure relate to sensor arrays, and more particularly to construction of modular sensor arrays.

Sensors or transducers are devices that transform input signals of one form into output signals of a different form. Commonly used transducers include light sensors, heat sensors, and acoustic sensors. A wide variety of various applications, such as biomedical non-invasive diagnostics and non-destructive testing (NDT) of materials entail the use of sensor arrays, where the sensors are often configured in two-dimensions (that is, the X-Y plane). Moreover, applications such as medical and industrial imaging, non-destructive testing (NDT) and inspection, security, baggage scanning, astrophysics and medicine may entail the use of sensors that encompass large areas. In the field of medical diagnostics, such as, but not limited to, X-ray, computed tomography (CT), ultrasound and mammography, it may be desirable to employ sensors that encompass large areas. For instance, in an X-ray imaging system, large area transducers may be useful to encompass the area of the X-ray detector. Moreover, in non-medical applications even larger arrays may be desired.

As noted hereinabove, large area detector arrays have desirable characteristics for certain applications. Sensor modules may be arranged to form the large area detector array. Furthermore, it is desirable that the edges of the sensor modules in the array are aligned with the edges of neighboring modules without any significant gaps or offsets. However, it is becoming increasingly difficult to achieve this tileable structure. Particularly, since the sensor detection element must be electrically connected to readout application specific integrated circuits (ASICs), the high density of interconnect requires a close correspondence between the ASIC contact pads and the sensor contact pads. Typically, the ASIC has contacts disposed on only one side. Furthermore, the ASIC in addition to using these contact pads to couple the ASIC to the sensor, also needs to use these contact pads to make power and digital communication connections to other system electronics. Therefore, it is desirable to implement some means of connecting both the sensor and system interconnects to this ASIC surface, while also supporting the four-sided tiling structure and a high pixel pitch in the sensor.

A currently available technique typically uses a staircase array of modules where a top surface of the ASIC is directly bonded to a bottom surface of the sensor element. This requires a match between the bump bond array on the ASIC and the bump bond array on the sensor. In addition the ASIC chip extends laterally beyond the sensor element and this extension is used to place wire bonds to couple the top surface of the ASIC to a backplane layer. Unfortunately, this extension of the ASIC creates a need to raise subsequent modules vertically to create a clearance space for the wire bonds. Additionally, all the modules in this detector array are not aligned in the same plane. These offsets disadvantageously create a non-ideal imaging geometry as the different modules are at different distances from an X-ray source. In particular, when the X-ray incident direction is not normal, there can be shadowing effects when one module occludes other modules.

Presently, certain other techniques entail forming the detector array by shingling sensor modules like roofing tiles or fish scales. In this embodiment, the extension of the sensor module and wire bonds is accommodated by the space created by the angle of the sensor modules. However, the module plane normal is not locally aligned to the detector plane normal since the edges of the sensor modules do not line up. This technique presents a non-ideal imaging geometry.

It would therefore be desirable to have a sensor module that allows assembly of large area detector arrays. Specifically, there exists a need for a detector array created by arranging a plurality of sensor modules as detailed herein. Furthermore, it is desirable to tile the sensor modules efficiently to form a high-density large area detector array in order to minimize system size, complexity, interconnect lengths and enhance the performance of the detector arrays.

BRIEF DESCRIPTION

In accordance with aspects of the present technique, a method for forming a sensor stack is presented. The method includes providing a substrate having a first side and a second side. Furthermore, the method includes disposing an integrated circuit having a first side and a second side on the first side of the substrate, where the integrated circuit comprises a first plurality of contact pads disposed on the first side of the integrated circuit. The method also includes providing a sensor array having a plurality of sensor elements, wherein each of the sensor elements has a first side and a second side, and wherein the sensor array includes a second plurality of contact pads disposed on a second side of the sensor array. Furthermore, the method includes disposing an interposer having one or more interposer elements and one or more through vias disposed therethrough between the one or more sensor elements of the sensor array and the integrated circuit to raise the sensor array away from the first side of the integrated circuit such that a plane of the one or more sensor elements is locally normal to a sensor stack normal, wherein the interposer is configured to operationally couple the second side of the sensor elements in the sensor array to the first side of the integrated circuit. In addition, the method includes operationally coupling the first plurality of contact pads on the first side of the integrated circuit to the second plurality of contact pads on the second side of the sensor array to form a tileable sensor stack.

In accordance with other aspects of the present technique, a method for forming a tileable detector array is presented. The method includes forming a tileable sensor stack, where forming the tileable sensor stack includes providing a sensor element having a first side and a second side, wherein the sensor element comprises a first plurality of contact pads disposed on the second side of the sensor element, disposing the sensor element on a portion of an area of an integrated circuit having a first side and a second side, disposing a wedge shaped interposer element between the sensor element and the integrated circuit, wherein the wedge shaped interposer element is configured to raise the sensor element away from the first side of the integrated circuit such that a plane of the sensor element is locally normal to a sensor stack normal, wherein the wedge shaped interposer element comprises through vias disposed therethrough, and wherein the interposer is configured to operationally couple the second side of the sensor element to the first side of the integrated circuit, operationally coupling the first plurality of contact pads on the second side of the sensor element to a second plurality of contact pads on the first side of the integrated circuit to form the tileable sensor stack. Additionally, the method includes tiling a plurality of tileable sensor stacks on a first side of a substrate to form the tileable detector array.

In accordance with further aspects of the present technique, a method for forming a tileable detector array is presented.

The method includes forming a first plurality of tileable stepped sensor stacks, where forming the first plurality of stepped sensor stacks includes providing a sensor element having a first side and a second side, wherein the sensor element comprises a first plurality of contact pads disposed on the second side of the sensor element, disposing the sensor element on a portion of an area of an integrated circuit having a first side and a second side, disposing an stepped interposer element between the sensor element and the integrated circuit, wherein the stepped interposer element is configured to raise the sensor element away from the first side of the integrated circuit such that a plane of the sensor element is locally normal to a sensor stack normal, wherein the stepped interposer element comprises through vias disposed therethrough, and wherein the stepped interposer element is configured to operationally couple the second side of the sensor element to the first side of the integrated circuit, operationally coupling the first plurality of contact pads on the second side of the sensor element to a second plurality of contact pads on the first side of the integrated circuit to form the first plurality of tileable stepped sensor stacks. Furthermore, the method includes forming a second plurality of sensor stacks, where forming the second plurality of sensor stacks includes providing a sensor element having a first side and a second side, wherein the sensor element comprises a first plurality of contact pads disposed on the second side of the sensor element, disposing the sensor element on a portion of an area of an integrated circuit having a first side and a second side, operationally coupling the first plurality of contact pads on the second side of the sensor element to a second plurality of contact pads on the first side of the integrated circuit to form the second plurality of tileable stepped sensor stacks. In addition, the method includes tiling the first plurality of tileable stepped sensor stacks and the second plurality of tileable stepped sensor stacks on a first side of a substrate to form the tileable detector array.

In accordance with yet another aspect of the present technique, a detector array is presented. The detector array includes a substrate having a first side and a second side. Furthermore, the detector array includes a plurality of tileable sensor stacks arranged on the first side of the substrate to form a planar detector array, wherein each of the plurality of tileable sensor stacks includes a sensor element having a first side and a second side, wherein the sensor element comprises a first plurality of contact pads disposed on the second side of the sensor element, an integrated circuit having a first side and a second side, an interposer element having one or more through vias disposed therethrough, wherein the interposer element is disposed between the sensor element and the integrated circuit and configured to raise the sensor array away from the first side of the integrated circuit such that a plane of the sensor element is locally normal to detector array normal, and wherein the interposer element is configured to operationally couple the second side of the sensor element to the first side of the integrated circuit, wherein the first plurality of contact pads on the second side of the sensor element is operationally coupled to a second plurality of contact pads on the first side of the integrated circuit to form the tileable sensor stack.

DRAWINGS

These and other features, aspects, and advantages of the present invention will become better understood when the following detailed description is read with reference to the accompanying drawings in which like characters represent like parts throughout the drawings, wherein:

FIG. 4 is a diagrammatic illustration of a method of forming a sensor stack having a wedge shaped interposer element, in accordance with aspects of the present technique;

FIG. 5 is a diagrammatic illustration of a method of forming a flat detector array using a plurality of the sensor stacks of FIG. 4, in accordance with aspects of the present technique;

FIGS. 9-11 are diagrammatic illustrations of different embodiments of stepped sensor stacks for use in forming the planar detector array of FIG. 8, in accordance with aspects of the present technique;

DETAILED DESCRIPTION

As will be described in detail hereinafter, systems and methods for forming detector arrays and various embodiments of large area detector arrays are presented. By employing the methods and detector arrays described hereinafter, a large area planar or arc detector array with a locally smooth surface is formed.

Although, the exemplary embodiments illustrated hereinafter are described in the context of a detector array configured for use in a computed tomography (CT) imaging system, it will be appreciated that use of the detector array in other imaging systems, such as, but not limited to an X-ray imaging system, an ultrasound imaging system, a magnetic resonance (MR) imaging system, a positron emission tomography (PET) imaging system, a single photon emission computed tomography (SPECT) imaging system and the like are also contemplated in conjunction with the present technique. Furthermore, use of the detector array in other applications such as equipment diagnostics and inspections, baggage inspections, and security applications is also envisaged.

Figure 1:
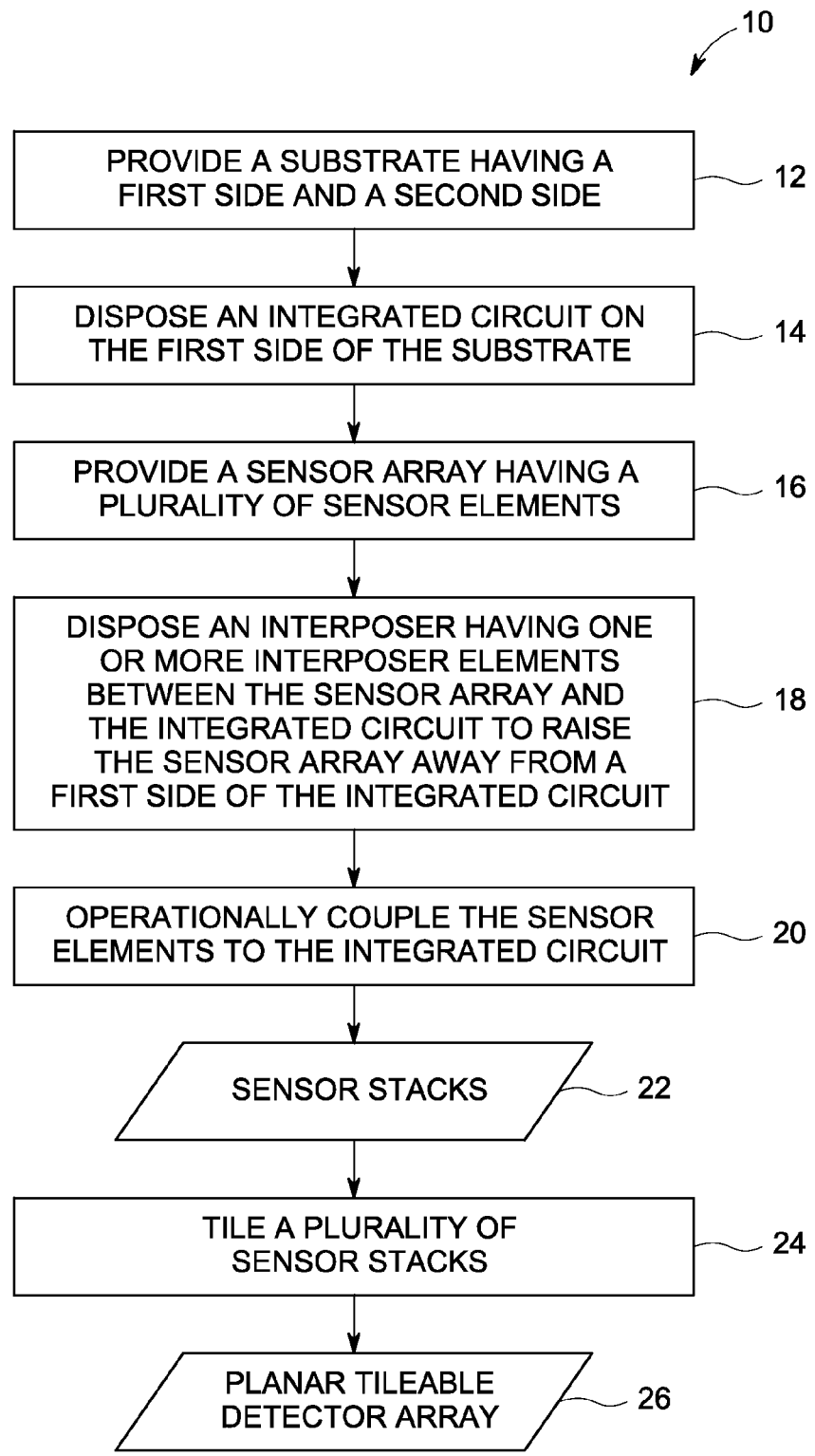
FIG. 1 is a diagrammatic illustration of a method for forming a detector array, in accordance with aspects of the present technique.

Turning now to the drawings, and referring to FIG. 1, a flow chart 10 illustrating exemplary logic of a method of forming a tileable planar detector array for use in a system, such as, but not limited to an X-ray imaging system or a CT imaging system, is depicted. The detector array so formed may be used to sense a plurality of input signals. As used herein, the term "detector array" is used to refer to a determined arrangement of sensor stacks. Furthermore, it may be noted that in one embodiment, the term "planar detector array" is used to refer to a detector array that is formed by arranging a plurality of sensor stacks such that the plane of the sensor stacks is locally normal to the detector normal and the detector array has a locally smooth surface. It may further be noted that the planar detector array may include a flat panel detector array or an arc detector array. Also, as used herein, the term "sensor array" is used to refer to an arrangement of one or more sensors or sensor elements. In addition, the term "sensor stack" is used to refer to a stacked arrangement of at least one sensor element, an integrated circuit, such as an ASIC, and an interposer element disposed therebetween.

As illustrated in FIG. 1, the method starts at step 12, wherein a substrate is provided. The substrate has a first side and a second side. Also, the substrate may be a rigid substrate or a flexible substrate. In one embodiment, the rigid substrate may be formed using high-density organic materials such as a multi-layered substrate made of expanded TEFLON, such as Rogers 2800, FR4 or BT laminate materials. Alternatively, an inorganic material such as ceramic (96% Alumina) or a Si interposer may be employed to form the rigid substrate. Furthermore, the flexible substrate may be formed using polyimide thin films. Moreover, the substrate may be representative of a backplane layer that includes other system electronics, in certain embodiments.

Subsequently, as depicted by step 14, one or more integrated circuits having a respective first side and a second side are disposed on the first side of the substrate. Particularly, the second sides of the one or more integrated circuits are coupled to the first side of the substrate. In one embodiment, the one or more integrated circuits may be coupled to the substrate using conventional assembly methods such as wire bonding or flip chip attach. It may be noted that in certain embodiments, the one or more integrated circuits may include an application specific integrated circuit (ASIC). Furthermore, a plurality of contact pads is disposed on the first side of each of the one or more integrated circuits. These contact pads aid in coupling the integrated circuits to one or more sensor elements. Additionally, these contact pads also facilitate power and/or digital communication connections from the integrated circuits to other system electronics, such as the system electronics in the substrate.

Furthermore, at step 16, a sensor array is provided. As previously noted, the term "sensor array" is used to refer to a patterned arrangement of one or more sensor elements, where the one or more sensor elements are configured to detect input signals, such as radiation signals, acoustic signals, light signals, and the like. Each of the one or more sensor elements has a respective first side and a second side. In certain embodiments, the first side of the one or more sensor elements is configured to receive the input signals. Also, a plurality of contact pads is disposed on the second side of each sensor element. It may be noted that in some embodiments, each sensor element may have only one contact pad disposed on the second side. These contact pads are employed to operationally couple the sensor elements in the sensor array to the integrated circuit.

As described hereinabove, it is desirable to form a substantially planar detector array in which the sensor elements are assembled on one side of the substrate and the one or more integrated circuits (IC) are assembled on the other side of the substrate to form a tileable module. An array of these modules may then be assembled to the next level of carrier to produce a larger sensor array. In accordance with aspects of the present technique, the shortcomings of the presently available techniques may be circumvented via use of an interposer to form a substantially planar detector array. As will be appreciated, an interposer is an electrical interface routing between one connection to another. Particularly, the purpose of the interposer in one example is to spread a connection to a different pitch or to reroute a connection to a different connection. It may be noted that in certain embodiments the interposer may be a rigid interposer, while in certain other embodiments, the interposer may be a flexible interposer. By way of example, the rigid interposer may include a FR4 material, while the flexible interposer may include a polyimide. Additionally, the interposer may include a ceramic material or an organic material.

Particularly, in accordance with aspects of the present technique, an interposer is used to facilitate creation of a substantially planar detector array. More specifically, an interposer having one or more interposer elements is disposed between the one or more sensor elements in the sensor array and the one or more integrated circuits, as depicted by step 18. The interposer elements are configured to operationally couple the sensor elements to respective integrated circuits. Furthermore, a plurality of top contact pads are disposed on the first side of the interposer, where these contact pads are configured to operationally couple the interposer to the contact pads disposed on the second side to the sensor elements in the sensor array. Moreover, a plurality of bottom contact pads are disposed on the second side of the interposer, where the bottom contact pads are configured to couple the interposer to the contact pads disposed on the first side of the integrated circuits.

Additionally, in accordance with further aspects of the present technique, the interposer so disposed between the sensor elements and the integrated circuits aids is raising the sensor array away from the first side of the integrated circuits, thereby creating a clearance space between the sensor array and the integrated circuit. Wire bonds and/or other flexible interconnect that are used to operationally couple the integrated circuits to other electronics may be disposed in the clearance space between the sensor array and the integrated circuits created by the use of the interposer.

Furthermore, in accordance with further aspects of the present technique, the interposer elements include one or more through vias disposed therethrough. Also, in one embodiment, the through vias may include through silicon vias (TSVs). As will be appreciated, a through silicon via is a vertical connection that passes completely through a silicon wafer or die and is configured to aid in coupling devices in a package while reducing the footprint of the package. In the present embodiment, the TSVs in the interposer elements allow for power signals, ground signals, analog signals and/or digital signals to be routed directly from the sensor array through the TSVs to the integrated circuits. Specifically, these vias are used to route any connections between the sensor elements in the sensor array and the integrated circuits.

Moreover, in one embodiment, the interposer may be formed using a multilayer ceramic material. The interposer may include one or more lateral routing layers, where the lateral routing layers are configured to aid in pitch adaptation in which the substrate can interconnect the input/output (I/O) pads of the IC die with the corresponding elements on the sensor. Also, the interposer may include one or more lateral routing traces, where the lateral routing traces are configured to aid in coupling the top contact pads to the bottom contact pads on the interposer. These lateral routing traces may include metalized traces, in certain embodiments.

Moreover, in accordance with exemplary aspects of the present technique, the interposer includes interposer elements having a varying thickness. By way of example, the thickness of the interposer elements may be varied based on a thickness required to form a substantially planar detector array. Particularly, the thickness of the interposer element corresponding to a sensor element may be varied to ensure that the sensor element is disposed in the same plane as the other sensor elements in the detector array. It may be noted that based on a level of a sensor element in the planar detector array, some sensor elements in the sensor array may not entail use of an interposer element to elevate the sensor element.

In accordance with further aspects of the present technique, the interposer may include interposer elements having a square shape or a rectangular shape. In certain other embodiments, the interposer elements may have a wedge shape. It may be noted that although the interposer elements are described as having square, rectangular or wedge shapes, other shapes of the interposer elements are also envisaged. These embodiments will be described in greater detail with reference to FIGS. 4-11.

The sensor elements in the sensor array are then operationally coupled to the one or more integrated circuits employing the one or more interposer elements, as indicated by step 20. Particularly, the contact pads on the second side of the sensor elements are coupled to the top contact pads on the first side of the interposer. In some embodiments, the contact pads on the second side of the sensor elements are coupled to the top contact pads on the first side of the interposer using either flip chip attach (FCA) or wire bonding of the ASIC die. In the case of FCA, a full area array of I/O pads may be used for coupling the sensor elements to the interposer. However, in the case of wire bonding, a perimeter array of I/O pads may be used to couple the sensor elements to the interposer. Additionally, at step 20, the integrated circuits are coupled to the interposer elements by attaching the bottom contact pads on the second side of the interposer to the contact pads on the first side of the integrated circuits. In certain embodiments, the contact pads on the second side of the sensor elements are coupled to the top contact pads on the first side of the interposer using an area array assembly process. In the case of a Si device, a FCA process is typically used. However, variations of this process entail use of a gold-stud bump on the die surface along with silver-fill conductive epoxy, which can be carried out at substantially lower temperatures than conventional solder FCA methods. Also, if a sensor element is not associated with an interposer element, that sensor element may be directly coupled to the corresponding integrated circuit.

Consequent to the processing of steps 12-20, a plurality of sensor stacks 22 is formed. Accordingly, in certain embodiments, the method of forming the detector array includes forming a plurality of sensor stacks 22. Specifically, an interposer element of a desired thickness is disposed between a sensor element and an integrated circuit to form a sensor stack 22. This stacking of the sensor element, the interposer element and the integrated circuit allows creation of the sensor stack 22 with four-sided tileability. Particularly, the sensor stack 22 allows the first side of the integrated circuit to be coupled to the second side of the sensor element. Additionally, the sensor stack 22 also allows the same first side of the integrated circuit to be coupled to other system electronics.

The sensor stacks 22 with four-sided tileability so formed may then be arranged in determined pattern on a first side of a substrate, as indicated in step 24. Specifically, the sensor stacks 22 may be tiled on the first side of the substrate to form a substantially planar detector array. Once the sensor stacks 22 are arranged in a determined pattern to form a substantially planar detector array, the integrated circuits are coupled to the other system electronics. In one embodiment, wire bonds may be used to operationally couple the integrated circuits to the other system electronics.

Subsequent to steps 12-24, a substantially planar detector array 26 is formed. The four-sided tileability of the sensor stacks 22 allows the sensor stacks 22 to be tiled on the substrate to form the substantially planar detector array 26 that is constructed with sensor stacks 22 that are all disposed in the same plane. In addition, these sensor stacks 22 allow creation of detector arrays of different geometries while maintaining a small pitch sensor.

Figure 2:
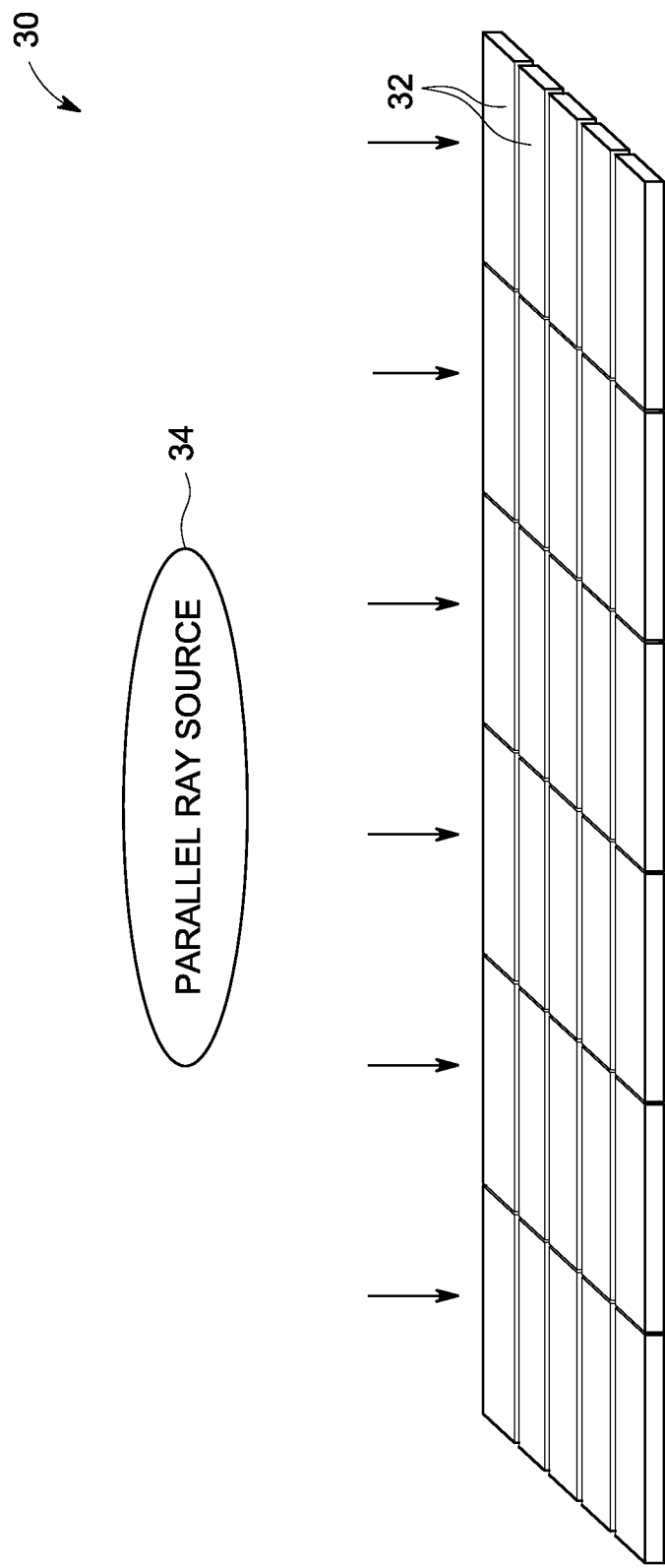
FIG. 2 is a diagrammatic illustration of an embodiment of a planar detector array formed using sensor modules that include a stepped interposer or a wedge shaped interposer, in accordance with aspects of the present technique.

FIG. 2 depicts a diagrammatic illustration of one embodiment 30 of a substantially planar detector array formed employing the method of FIG. 1. Particularly, FIG. 2 depicts a flat panel detector array 30 that is configured for use with a parallel ray source 34. The flat panel detector array 30 is constructed by tiling an array of sensor stacks 32, such as the sensor stacks 22 (see FIG. 1). More specifically, the sensor stacks 32 are tiled such that the sensor elements in the sensor array are all in the same plane. The substantially planar detector array 30 depicted in FIG. 2 may be configured for use in an X-ray imaging system, for example.

Figure 3:
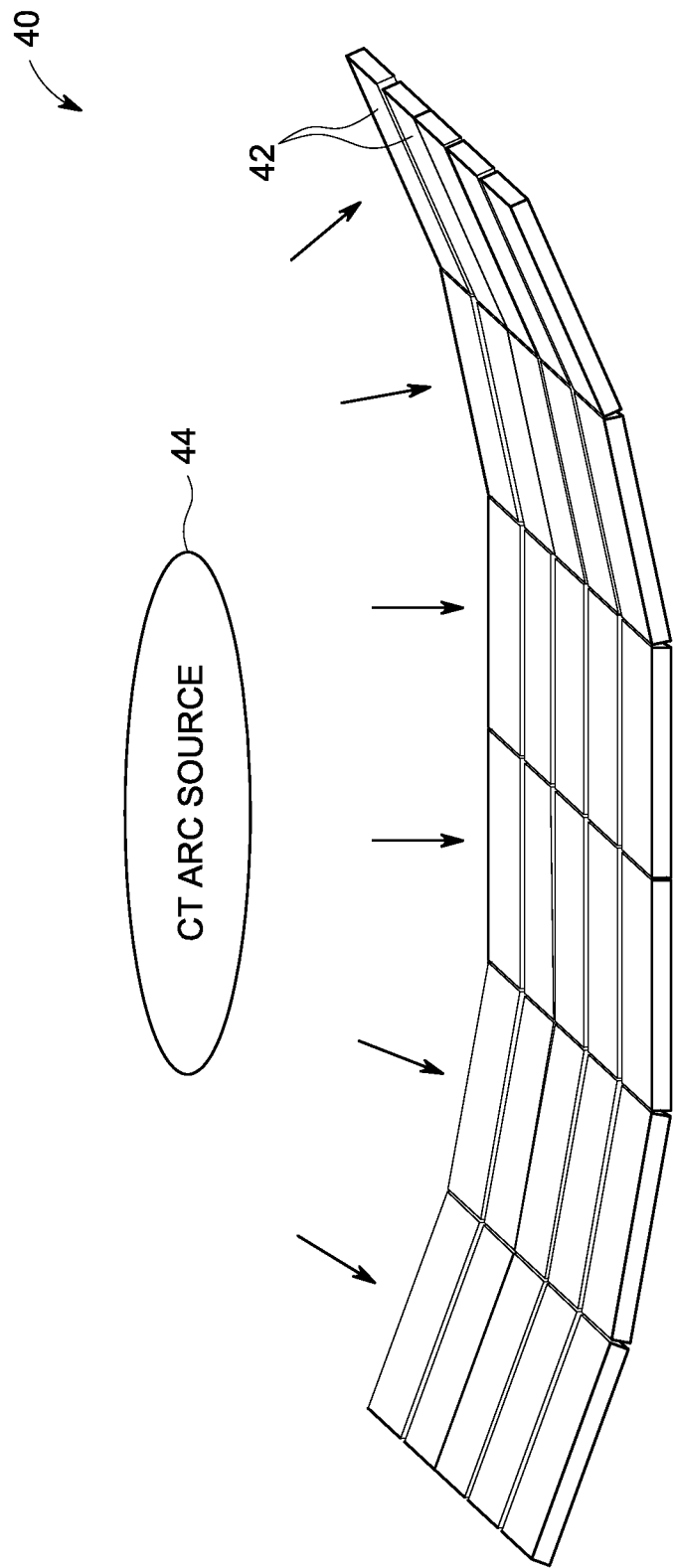
FIG. 3 is a diagrammatic illustration of an embodiment of an arc detector array formed using sensor modules that include a stepped interposer or a wedge shaped interposer, in accordance with aspects of the present technique.

Referring now to FIG. 3, an embodiment 40 of an arc detector array is depicted. In particular, the arc detector array 40 is representative of a locally flat array of sensor stacks 42 configured for use such as a CT arc detector. Reference numeral 44 is generally representative of a CT arc source. Here again, the detector array 40 is formed by arraying a plurality of sensor stacks 42, such as the sensor stacks 22 of FIG. 1. It may be noted that although the sensor stacks 42 are not disposed in the same plane globally, the edges of the sensor stacks 42 are lined up without offsets or with minimal offsets to form a smooth curve of the arc detector array 40.

As noted hereinabove, the substantially planar detector array is formed by tiling a plurality of sensor stacks. Furthermore, the sensor stacks may include an interposer element. In one example, the interposer element is configured to aid is raising the sensor element away from the integrated circuit, thereby creating a clearance space. The interposer element also facilitates coupling the sensor element to the integrated circuit.

Turning now to FIG. 4, one embodiment 50 of an exemplary sensor stack for use in forming a substantially planar detector array is illustrated. In a presently contemplated configuration, the sensor stack 50 includes a sensor element 52 disposed on an integrated circuit 54. Specifically, the sensor element 52 is disposed on the integrated circuit 54 such that an area of the sensor element 52 covers only a portion of an area of the integrated circuit 54.

In accordance with aspects of the present technique, an interposer element 56 configured to couple the sensor element 52 to the integrated circuit 54 is disposed between the sensor element 52 and the integrated circuit 54. The interposer element 56 in the embodiment of FIG. 4 includes a wedge shaped interposer element. As used herein, the term "wedge shaped interposer element" is used to refer to an interposer element that has an angled profile. In one example, the wedge shaped interposer element has at least one trapezoidal cross-section. Particularly, the interposer element 56 has a first thickness at a first end and a second thickness at a second end, where the first thickness is different from the second thickness. By way of example, the first thickness may be less than the second thickness. Also, in one embodiment, the wedge shaped interposer element 56 is formed using a ceramic material. In certain other embodiments, the wedge shaped interposer element 56 may be formed using semiconductor materials and/or polymetric materials. Particularly, in each case the material used to form the wedge shaped interposer element 56 has a mechanical function to support the sensor element in a detector array with the intended impact to overall geometry of the detector array. Also, the material is selected such that the material allows adaptation of electrical interconnects between the sensor contact and the readout electronics.

As previously noted, the sensor element 52 has one or more contact pads disposed on a second side. Also, a first side of the integrated circuit 54 has one or more contact pads disposed thereon. Furthermore, the interposer element 56 aids in coupling the sensor element 52 to the integrated circuit 54 using contact pads disposed on a first side and a second side of the interposer element 56. Additionally, in accordance with aspects of the present technique, the interposer element 56 includes one or more through vias (not shown in FIG. 4) disposed therethrough. The interposer element 56 also may include one or more lateral routing traces and/or one or more lateral routing layers (not shown in FIG. 4). The interposer element 56 will be described in greater detail with reference to FIGS. 6-7.

Disposing the wedge shaped interposer element 56 between the sensor element 52 and the integrated circuit 54 aids in raising the sensor element 52 away from the integrated circuit 54, thereby creating a clearance space 58 between the sensor element 52 and the integrated circuit 56. Any interconnect configured to couple the integrated circuit 54 to other system electronics (not shown in FIG. 4) may be disposed in this clearance space 58. In one embodiment, the interconnect may include a wire bond 62 that couples the integrated circuit 54 to other electronics that may be disposed in a substrate 60. It may also be noted that use of the wedge shaped interposer element 56 in the sensor stack 50 advantageously allows the first side of the integrated circuit 54 to be operationally coupled to the second side of the sensor element 52 while also permitting coupling of the same first side of the integrated circuit 54 to other system electronics.

Additionally, the sensor stack 50 may also include a spacer element 64. Specifically, in the illustrated embodiment of FIG. 5, the spacer element 64 is disposed between the second side of the integrated circuit 54 and a first side of the substrate 60 that the sensor stack 50 is disposed on. Also, in one embodiment, the spacer element 64 includes a wedge shaped spacer element. The spacer element 64 is configured to compensate geometrically for the wedge shaped interposer element 56 so that the substrate 72 is also in a single plane. A simplifying feature of the spacer element 64 is that it does not provide any electrical interconnects and provides only a mechanical function. Moreover, the spacer element 64 is formed using polymetric materials, metals or ceramic materials.

The sensor stack 50 so formed advantageously creates the clearance space 58 where interconnects, such as flexible interconnects and/or wire bonds may be disposed, thereby reducing the footprint of the sensor stack 50. Also, the sensor stack 50 creates a sensor stack with four-sided tileability that allows implementation of various geometries of detector arrays while maintaining a small pitch.

As previously noted, it is desirable to form substantially planar large area detector arrays, such as the detector arrays 30 (see FIG. 2) and 40 (see FIG. 3), for use in applications such as but not limited to imaging systems and security screening applications. In accordance with aspects of the present technique, a plurality of sensor stacks, such as the sensor stacks 50 of FIG. 4 are tiled to form a large area substantially planar detector array.

FIG. 5 depicts one embodiment 70 of a substantially planar large area detector array. Particularly, a plurality of sensor stacks 50 (see FIG. 4) is tiled on a first side of a substrate 72. The substrate 72 may be a flexible substrate or a rigid substrate. Also, the substrate 72 may be formed employing circuit boards materials such as FR4, BT-Epoxy, CEM-1,5, TEFLON, polytetrafluoroethylene (PTFE) or polyimide. The plurality of sensor stacks 50 is arranged on the substrate 72 in a determined pattern based on an application. The four-sided tileability of the sensor stacks 50 permits tiling of the plurality of sensor stacks 50 on the substrate 72 to form the substantially planar detector array 70. As previously noted, use of the wedge shaped interposer element 56 raises the sensor element 52 away from the integrated circuit 54 thereby creating the clearance space 58. Wire bonds 74 and other flexible interconnects (not shown in FIG. 5) are disposed in this clearance space 58. The wire bonds 74 and/or other interconnect are employed to couple the integrated circuit 54 to other system electronics that may be disposed in the substrate 72.

Tiling the plurality of sensor stacks 50 having the wedge shaped interposer elements 56 on the substrate 72 aids in creating a substantially planar detector array 70. Furthermore, use of the interposer element 56 having through vias disposed therethrough in the sensor stack 50 facilitates coupling the first side of the integrated circuit 54 to the second side of the sensor element 52. It may be noted that a high pitch may be maintained using the wedge shaped interposer element 56. Additionally, use of the interposer element 56 circumvents the need for an exact match between the array of contact pads on the first side of the integrated circuit 54 and the array of contact pads of the second side of the sensor element 52. In addition, the interposer element 56 covers only a portion of the integrated circuit area and also raises the sensor element 52 away from the first side of the integrated circuit 54. These partial-coverage and spacing-away features create a clearance space 58 in the tiled detector array structure where wire bonds 74 or some other flexible interconnect can attach the surface of the integrated circuit 54 to the system electronics. In this way the interconnect needs are met while still providing four-sided tileability with a fine pitch sensor.

Figure 6:
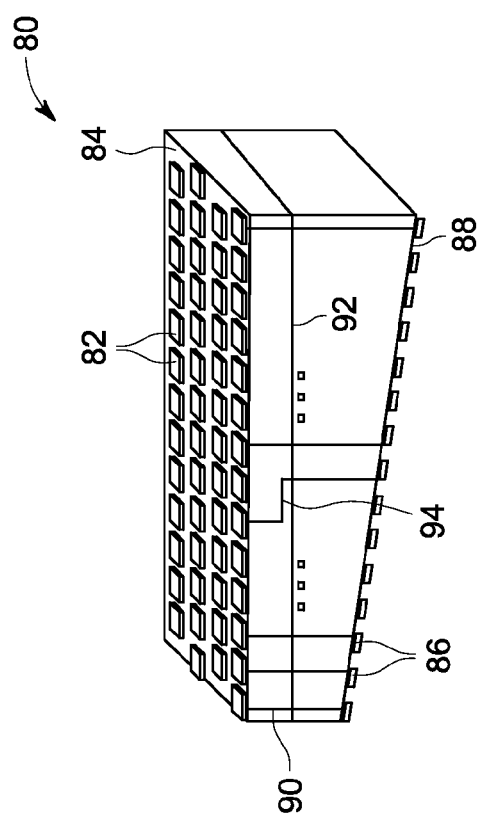
FIG. 6 is a diagrammatic representation of one embodiment of wedge shaped interposer having through vias disposed therethrough and configured for use in the detector modules of FIGS. 2 and 3, in accordance with aspects of the present technique.

Referring now to FIG. 6, a cross-sectional view 80 of a wedge shaped interposer element, such as the wedge shaped interposer element 56 of FIG. 4 configured for use in the detector arrays of FIGS. 2 and 3 is depicted. As previously noted, the wedge shaped interposer element 80 is formed using a multilayer ceramic material, a semiconductor material or other polymetric materials. Also, as described hereinabove, the interposer element 80 is configured to operationally couple a sensor element, such as the sensor element 52 (see FIG. 4) to an integrated circuit, such as the integrated circuit 54 (see FIG. 4). To that end, the interposer element 80 includes a first plurality contact pads 82 disposed on a first side 84 of the interposer element 80. The first plurality of contact pads 82 is configured to couple the first side 84 of the interposer element 80 to the contact pads disposed on the second side of the sensor element. Additionally, a second plurality contact pads 86 is disposed on a second side 88 of the interposer element 80, where the second plurality of contact pads 86 is configured to operationally couple the second side 88 of the interposer element 80 to the contact pads disposed on the first side of the integrated circuit. It may be noted that the first and second pluralities of contact pads 82 and 86 may be attached to the first side 84 and the second side 88 of the interposer element 80 respectively using a solder, compressive displacement or conductive adhesive attach process.

Furthermore, the arrangement of the contact pads 82 and 86 on the first and second sides 84, 88 of the interposer element 80 is configured to adapt the layout of contact pads on the first side of the integrated circuit to the layout of the contact pads on the second side of the sensor element using one or more through vias 90 and/or one or more lateral routing layers 92 in the interposer element 80. In one embodiment, the through vias 90 may include through silicon vias (TSVs), as previously noted. In the present embodiment, the TSVs 90 in the interposer element 80 allow for power signals, ground signals, analog signals and/or digital signals to be routed directly from the sensor element through the TSVs 90 directly under the die. Additionally, the lateral routing layers 92 are configured to provide greater flexibility in routing design such that the contacts 82 and 86 are laterally positioned to match the desired configuration of the contacts on the to contact pads on the ASIC die. Moreover, reference numeral 94 is generally representative of lateral routing traces configured to aid in coupling the first plurality of contact pads 82 to the second plurality of contact pads 86. These traces may include metalized traces, in one embodiment.

It may further be noted, that if the interposer element 80 includes only through vias 90 disposed therethrough, then it is desirable that the layout of the contact pads on the second side of the sensor element be substantially similar to the layout of contact pads disposed on the first side of the integrated circuit. However, if the interposer element 80 includes the lateral routing layers 92 in addition to the through vias 90, then the interposer element 80 may be configured to couple a disparate arrangement of contact pads of the sensor element to the contact pads of the integrated circuit.

As previously noted, the wedge shaped interposer element 80 is configured to raise the sensor element away from the integrated circuit thereby creating a clearance space between the sensor element and the integrated circuit that can be utilized to position any interconnect, such as wire bonds. To that end, in accordance with other aspects of the present technique, a wedge angle of the wedge shaped interposer element 80 is determined. As used herein, the term "wedge angle" is used to refer to an inclination formed by two sides of the wedge shaped interposer element 80. Particularly, the wedge angle is determined based on an angle that is required on the wedge shaped interposer element to create a desired clearance space for the wire bonds corresponding to a desired clearance height and width of the sensor stack.

Figure 7:
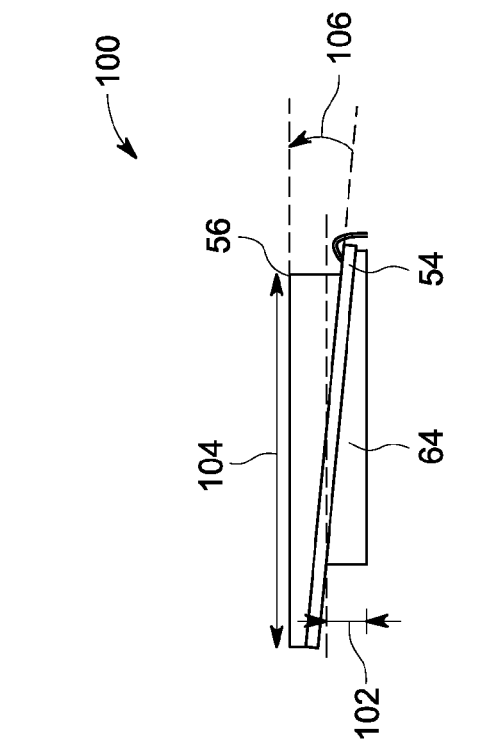
FIG. 7 is a diagrammatic illustration of computation of a wedge angle for the wedge shaped interposer of FIG. 6, in accordance with aspects of the present technique.

FIG. 7 depicts a diagrammatic illustration 100 of the computation of a wedge angle for the interposer element 80 (see FIG. 6). In accordance with aspects of the present technique, the wedge angle a 106 may be computed using the following equation:

$$c = w * \tan(a) \quad (1)$$

where c is a clearance height 102 and w is the width 104 of the sensor stack.

By way of example, if a desired clearance height 102 of a sensor stack is 0.5 mm and a desired width 104 of the sensor stack is 8 mm, the desired wedge angle a 106 is computed using equation (1) to have a value of 3.6 degrees.

In the embodiment of the substantially planar detector array 70 depicted in FIG. 5, each sensor stack 50 is substantially similar to the other sensor stacks in the detector array 70. Particularly, each sensor stack 50 includes a sensor element, a wedge shaped interposer element and an integrated circuit stacked to form the sensor stack 50. Furthermore, since this embodiment of the detector array 70 entails use of substantially similar stacks 50, the efficiency of the detector array 70 is enhanced. Additionally, the cost of forming this detector array 70 is reduced since the creation of the detector array 70 entails use of substantially similar sensor stacks 50.

According to further aspects of the present technique, a substantially planar detector array may also be formed using a plurality of stepped sensor stacks. As used herein, the term "stepped sensor stacks" is used to refer to sensor stacks that include interposer elements and/or spacer elements of different thicknesses. Also, in some embodiments, the stepped sensor stack may include a sensor element, an interposer, an integrated circuit and a spacer element, while in certain other embodiments, the stepped sensor stack may include only a sensor element, an interposer element and an integrated circuit.

Figure 8:
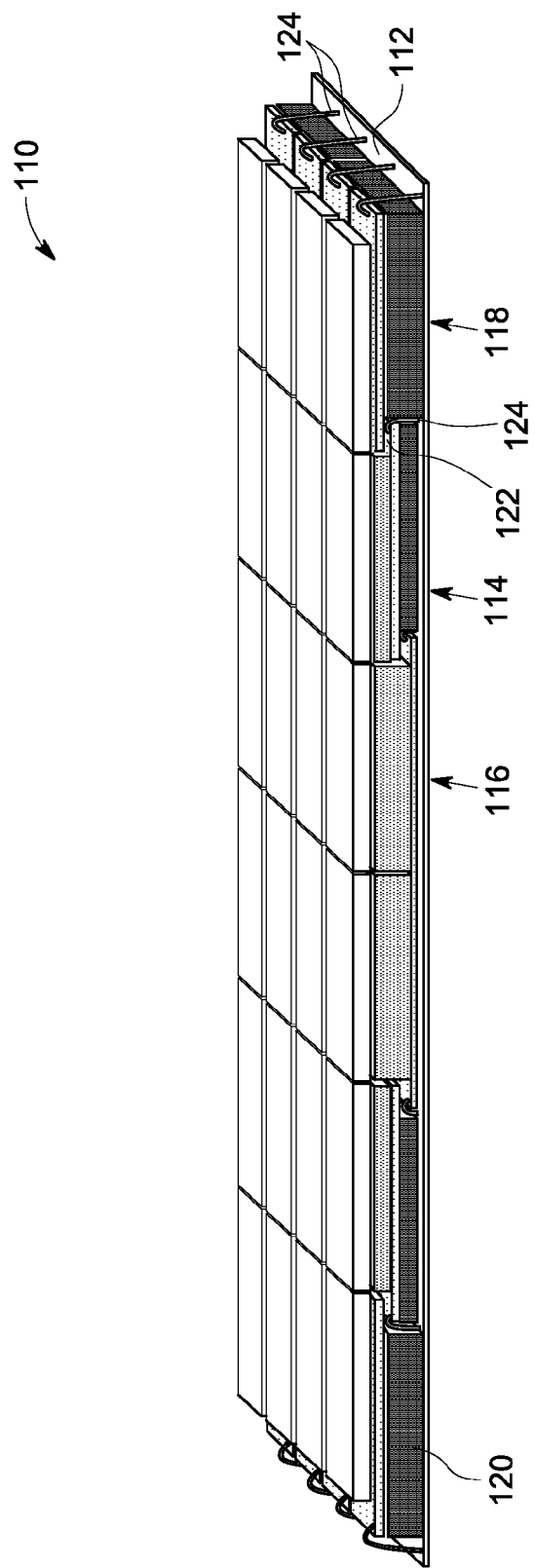
FIG. 8 is a diagrammatic illustration of a method of forming a planar detector array employing a plurality of stepped sensor stacks having a stepped interposer element, in accordance with aspects of the present technique.

Turning now to FIG. 8, another embodiment of a substantially planar detector array 110 is depicted. Particularly, the detector array 110 of FIG. 8 is formed by tiling a first plurality of stepped sensor stacks and a second plurality of stepped sensor stacks on a first side of a substrate 112. As used herein, the term "first plurality of stepped sensor stacks" is used to refer to a sensor stack that includes a sensor element that is indirectly coupled to an integrated circuit using an interposer element disposed therebetween. In this sensor stack, the element has a substantially square or rectangular shape. Further, the term "second plurality of stepped sensor stacks" is used to refer to a sensor stack that includes a sensor element that is directly coupled to an integrated circuit and does not include an interposer element disposed therebetween. In addition, the first and second pluralities of sensor stacks may also optionally include a spacer element, in certain embodiments. However, in certain other embodiment, the spacer element may be omitted.

With continuing reference to FIG. 8, reference numerals 114 and 116 are examples of the first plurality of stepped sensor stacks that include a sensor element, an integrated circuit and an interposer element disposed therebetween. Also, one example of the second plurality of stepped sensor stacks that includes a sensor element directly coupled to an integrated circuit but does not include an interposer element disposed therebetween is generally referenced by reference numeral 118.

In accordance with aspects of the present technique, the stepped sensor stacks 114 and 116 include interposer elements of varying thickness. Specifically, the sensor stack 114 includes an interposer element of a smaller thickness, while the sensor stack 116 includes an interposer element of a relatively greater thickness. According to aspects of the present technique, the thickness of the interposer elements is varied to facilitate formation of sensor stacks that aid in creating substantially planar detector arrays. Accordingly, the thickness of the interposer element is varied based on the thicknesses of the other elements in the sensor stack.

Furthermore, the stepped sensor stack 118 includes a sensor element that is directly coupled to the integrated circuit without the use of an interposer element. Moreover, the sensor stacks 114, 116 and 118 may optionally include a spacer element 120. The thickness of the spacer element 120 may be varied to aid in the creation of a substantially planar detector array. Also, use of the interposer element aids in raising the sensor element away from a surface of the integrated circuit, thereby creating a clearance space 122. Wire bonds 124 and/or other flexible interconnect used to couple the first side of the integrated circuit to other system electronics may be disposed in this clearance space 122.

FIGS. 9-11 depict various embodiments of the stepped sensor stacks that are employed to create the substantially planar detector array 110 (see FIG. 8). Referring now to FIG. 9, one embodiment of the sensor stack 114 is depicted. The sensor stack 114 includes a sensor element 132 disposed on a portion of an area of an integrated circuit 134. The sensor element 132 is operationally coupled to the integrated circuit 134 using an interposer element 136. In one example, the interposer element 136 is not wedge shaped, but may have a polygonal shape such as a square or a rectangle. Use of the interposer element 136 aids in raising the sensor element 132 away from a surface of the integrated circuit 134. The partial coverage of the area of the integrated circuit 134 by the sensor element 132 and the spacing away of the sensor element 132 from the integrated circuit 134 creates a clearance space 138 in the sensor stack 114. Wire bonds 140, such as wire bonds 124 of FIG. 8, and/or other flexible interconnect used to couple a first side of the integrated circuit 134 to other system electronics may be disposed in this clearance space 138. The sensor stack 114 is also shown as including a spacer element 142.

FIG. 10 depicts one embodiment of the sensor stack 116 of FIG. 8. The sensor stack 116 includes a sensor element 152 disposed on a portion of an area of an integrated circuit 154. In this embodiment, the sensor element 152 is operationally coupled to the integrated circuit 154 using an interposer element 156 that is relatively thicker than the interposer element 136 of FIG. 9. A clearance space 158 in the sensor stack 116 created by the partial coverage of an area of the integrated circuit 154 by the sensor element 152 and the spacing away of the sensor element 152 from a surface of the integrated circuit 154 is used to dispose wire bonds 160 to couple a first side of the integrated circuit 154 to other system electronics. It may be noted that this sensor stack 116 does not entail use of a spacer element.

Referring now to FIG. 11, one embodiment of the sensor stack 118 of FIG. 8, is depicted. The sensor stack 118 includes a sensor element 172 disposed on a portion of an area of an integrated circuit 174. In this embodiment, the sensor element 172 is directly coupled to the integrated circuit 174 without the use of an interposer element. A clearance space 178 in the sensor stack 118 created by the partial coverage of an area of the integrated circuit 174 by the sensor element 172 is used to dispose wire bonds 180 to couple the first side of the integrated circuit 174 to other system electronics. It may be noted that this sensor stack 118 entails use of a spacer element 176.

With returning reference to FIG. 8, the various embodiments of the sensor stacks 114 (see FIG. 9), 116 (see FIG. 10) and 118 (see FIG. 11) are representative of sensor stacks that allow four-sided tileability. Subsequently, these sensor stacks 114, 116, 118 are tiled in a determined pattern on the first side of the substrate 112 to form the substantially planar detector array 110. Tiling the plurality of sensor stacks 114, 116, 118 as described hereinabove ensures that the interconnect needs are met while still providing four-sided tileability with fine pitch sensor.

Figure 12:
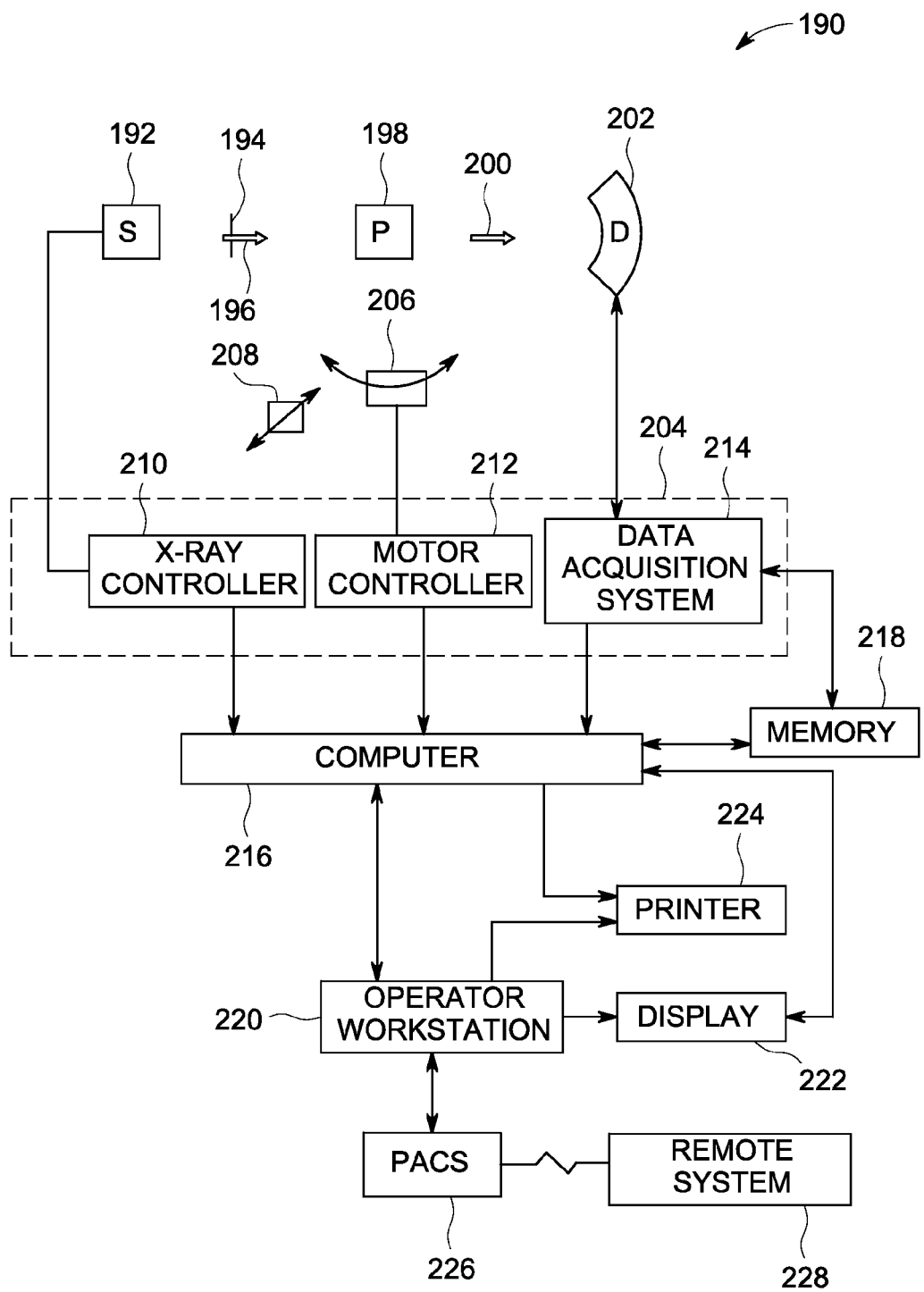
FIG. 12 is a block diagram of an exemplary imaging system in the form of a CT imaging system.

The flat panel detector array 30 of FIG. 2 and the arc detector array 40 of FIG. 3 may find application in a medical imaging system, such as a CT imaging system. FIG. 12 is a block diagram showing an imaging system 190 for acquiring and processing image data in accordance with the present technique. In the illustrated embodiment, the system 190 is a computed tomography system designed to acquire X-ray projection data, to reconstruct the projection data into an image, and to process the image data for display and analysis in accordance with the present technique. In the embodiment illustrated in FIG. 12, the imaging system 190 includes a source of X-ray radiation 192. In one exemplary embodiment, the source of X-ray radiation 192 may include an X-ray tube. The source of X-ray radiation 192 may include thermionic or solid-state electron emitters directed at an anode to generate X-rays or, indeed, any other emitter capable of generating X-rays having a spectrum and energy useful for imaging a desired object. Examples of suitable electron emitters include tungsten filament, tungsten plate, field emitter, thermal field emitter, dispenser cathode, thermionic cathode, photo-emitter, and ferroelectric cathode.

The source of radiation 192 may be positioned near a collimator 194, which may be configured to shape a stream of radiation 196 that is emitted by the source of radiation 192. The stream of radiation 196 passes into the imaging volume containing the subject to be imaged, such as a patient 198. The stream of radiation 196 may be generally fan-shaped or cone-shaped, depending on the configuration of the detector array, discussed below, as well as the desired method of data acquisition. A portion 200 of radiation passes through or around the subject and impacts a detector array, represented generally at reference numeral 202. Detector elements of the detector 202 produce electrical signals that represent the intensity of the incident X-ray beam. These signals are acquired and processed to reconstruct an image of the features within the subject.

The radiation source 192 is controlled by a system controller 204, which furnishes both power, and control signals for CT examination sequences. Moreover, the detector 202 is coupled to the system controller 204, which commands acquisition of the signals generated in the detector 202. The system controller 204 may also execute various signal processing and filtration functions, such as for initial adjustment of dynamic ranges, interleaving of digital image data, and so forth. In general, the system controller 204 commands operation of the imaging system 190 to execute examination protocols and to process acquired data. In the present context, the system controller 204 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 12, the system controller 204 is coupled via a motor controller 212 to a rotational subsystem 206 and a linear positioning subsystem 208. In one embodiment, the rotational subsystem 206 enables the X-ray source 192, the collimator 194 and the detector 202 to be rotated one or multiple turns around the patient 198. In other embodiments, the rotational subsystem 206 may rotate only one of the source 192 or the detector 202 or may differentially activate various stationary electron emitters to generate X-ray radiation and/or detector elements arranged in a ring about the imaging volume. In embodiments in which the source 192 and/or detector 202 are rotated, the rotational subsystem 206 may include a gantry (not shown in FIG. 12). Thus, the system controller 204 may be utilized to operate the gantry. The linear positioning subsystem 208 enables the patient 198, or more specifically a patient table (not shown in FIG. 12), to be displaced linearly. Thus, the patient table may be linearly moved within the gantry to generate images of particular areas of the patient 198.

Additionally, as will be appreciated by one skilled in the art, the source of radiation 192 may be controlled by an X-ray controller 210 disposed within the system controller 204. Particularly, the X-ray controller 210 is configured to provide power and timing signals to the X-ray source 192.

Further, the system controller 204 is also illustrated as including a data acquisition system 214. In this exemplary embodiment, the detector 202 is coupled to the system controller 204, and more particularly to the data acquisition system 214. The data acquisition system 214 receives data collected by readout electronics of the detector 202. The data acquisition system 214 typically receives sampled analog signals from the detector 202 and converts the data to digital signals for subsequent processing by a computer 216.

The computer 216 typically is coupled to or incorporates the system controller 204. The data collected by the data acquisition system 214 may be transmitted to the computer 216 for subsequent processing and reconstruction. The computer 216 may include or communicate with a memory 218 that may store data processed by the computer 216 or data to be processed by the computer 216. It may be noted that any type of memory configured to store a large amount of data might be utilized by the system 190. Moreover, the memory 218 may be located at the acquisition system or may include remote components, such as network accessible memory media, for storing data, processing parameters, and/or routines for implementing the techniques described below.

Additionally, the computer 216 may also be adapted to control features such as scanning operations and data acquisition that may be enabled by the system controller 204. Furthermore, the computer 216 may be configured to receive commands and scanning parameters from an operator via an operator workstation 220, which is typically equipped with a keyboard and other input devices (not shown). It may be noted that the operator workstation 220 may include a user interface, in certain embodiments. An operator, such as a clinician, may thereby control the system 190 via the input devices. Thus, the clinician may observe the reconstructed image and other data relevant to the system from computer 216, initiate imaging, and so forth.

A display 222 coupled to the operator workstation 220 may be utilized to observe the reconstructed images. Additionally, the scanned image may also be printed by a printer 224, which may be coupled to the operator workstation 220. The display 222 and the printer 224 may also be connected to the computer 216, either directly or via the operator workstation 220. The operator workstation 220 may also be coupled to a picture archiving and communications system (PACS) 226. It should be noted that PACS 226 might be coupled to a remote system 228, such as radiology department information system (RIS), hospital information system (HIS) or to an internal or external network, so that other clinicians at different locations may gain access to the image data.

It should be further noted that the computer 216 and operator workstation 220 may be coupled to other output devices, which may include standard or special purpose computer monitors and associated processing circuitry. One or more operator workstations 220 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, a virtual private network or the like.

Figure 13:
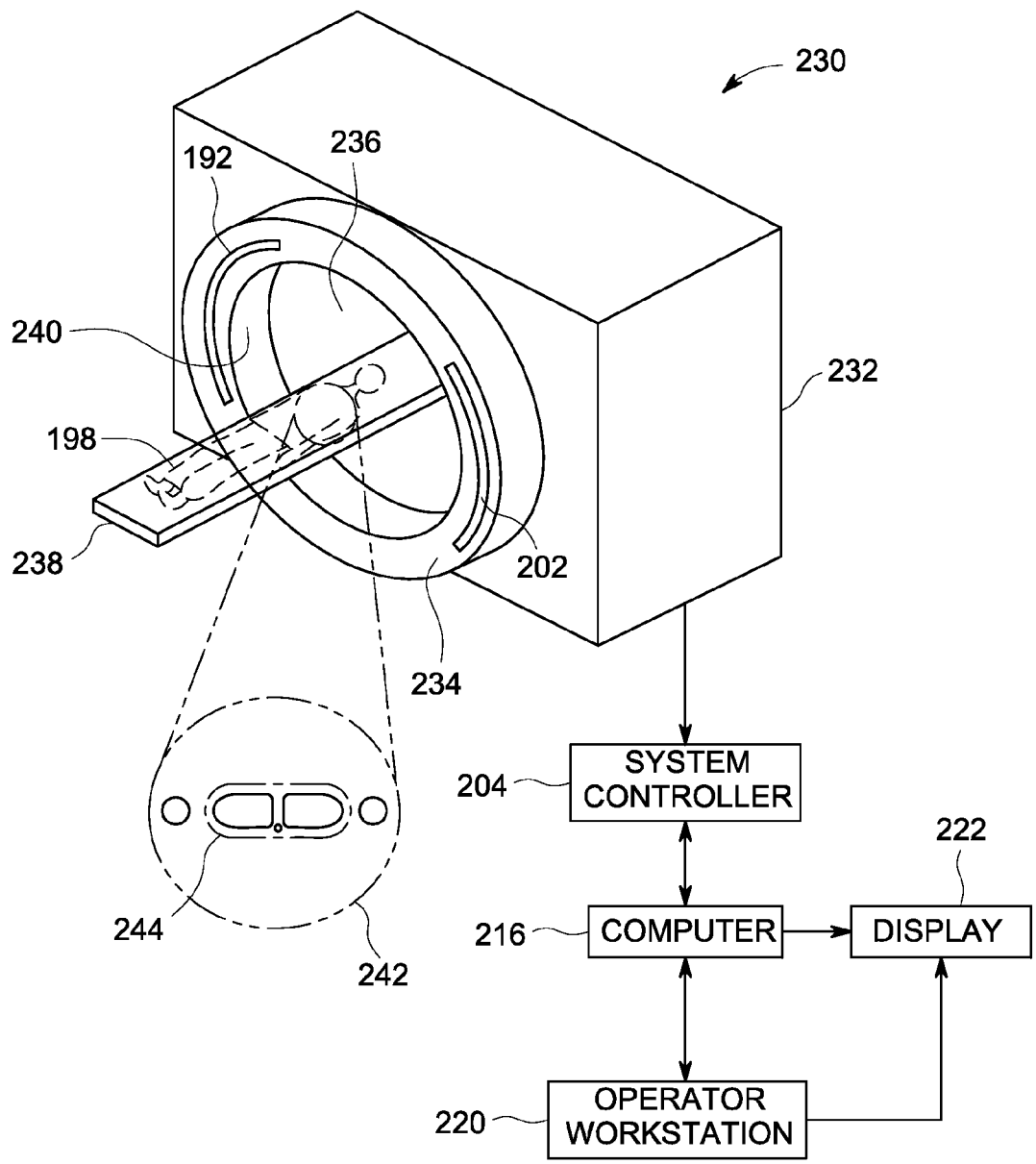
FIG. 13 is a block diagram of a physical implementation of the CT system of FIG. 12.

As noted above, an exemplary imaging system utilized in a present embodiment may be a CT scanning system 230, as depicted in greater detail in FIG. 13. The CT scanning system 230 may be a multi-slice CT (MSCT) system that offers a wide array of axial coverage, high rotational speed of the gantry, and high spatial resolution. Alternately, the CT scanning system 230 may be a volumetric CT (VCT) system utilizing a cone-beam geometry and an area detector to allow the imaging of a volume, such as an entire internal organ of a subject, at high or low gantry rotational speeds. The CT scanning system 230 is illustrated with a frame 232 and a gantry 234 that has an aperture 236 through which the patient 198 (see FIG. 12) may be moved. A patient table 238 may be positioned in the aperture 236 of the frame 232 and the gantry 234 to facilitate movement of the patient 198, typically via linear displacement of the table 238 by the linear positioning subsystem 208 (see FIG. 12). The gantry 234 is illustrated with the source of radiation 192, such as an X-ray tube that emits X-ray radiation from a focal point 240. For cardiac imaging, the stream of radiation is directed towards a cross section of the patient 198 including the heart.

In typical operation, the X-ray source 192 (see FIG. 12) projects an X-ray beam from the focal point 240 and toward the detector 202. The collimator 194 (see FIG. 12), such as lead or tungsten shutters, typically defines the size and shape of the X-ray beam that emerges from the X-ray source 192. The detector 202 is generally formed by a plurality of detector elements, which detect the X-rays that pass through and around a subject of interest, such as the heart or chest. Each detector element produces an electrical signal that represents the intensity of the X-ray beam at the position of the element during the time the beam strikes the detector. The gantry 234 is rotated around the subject of interest so that a plurality of radiographic views may be collected by the computer 216 (see FIG. 12).

Thus, as the X-ray source 192 and the detector 202 rotate, the detector 202 collects data related to the attenuated X-ray beams. Data collected from the detector 202 then undergoes pre-processing and calibration to condition the data to represent the line integrals of the attenuation coefficients of the scanned objects. The processed data, commonly called projections, may then be filtered and backprojected to formulate an image of the scanned area. A formulated image may incorporate, in certain modes, projection data for less or more than 360 degrees of rotation of the gantry 234.

Once reconstructed, the image produced by the system of FIGS. 12-13 reveals internal features 244 of the patient 198. In traditional approaches for the diagnosis of disease states, and more generally of medical conditions or events, a radiologist or physician typically consider the reconstructed image 242 to discern characteristic features of interest. In cardiac imaging, such features 244 include coronary arteries or stenotic lesions of interest, and other features, which would be discernable in the image, based upon the skill and knowledge of the individual practitioner. Other analyses may be based upon capabilities of various algorithms, including algorithms generally referred to as computer-aided detection or computer-aided diagnosis (CAD) algorithms.

Furthermore, the foregoing examples, demonstrations, and process steps such as those that may be performed by the imaging system 190, 230 may be implemented by suitable code on a processor-based system, such as a general-purpose or special-purpose computer. It should also be noted that different implementations of the present technique may perform some or all of the steps described herein in different orders or substantially concurrently, that is, in parallel. Furthermore, the functions may be implemented in a variety of programming languages, including but not limited to C++ or Java. Such code may be stored or adapted for storage on one or more tangible, machine readable media, such as on data repository chips, local or remote hard disks, optical disks (that is, CDs or DVDs), memory or other media, which may be accessed by a processor-based system to execute the stored code. Note that the tangible media may comprise paper or another suitable medium upon which the instructions are printed. For instance, the instructions may be electronically captured via optical scanning of the paper or other medium, then compiled, interpreted or otherwise processed in a suitable manner if necessary, and then stored in the data repository 248 or memory.

The methods for forming the substantially planar detector arrays and the various embodiments of the detector arrays described hereinabove dramatically enhance the ability to form two-dimensional high-density large area tileable detector arrays with a locally smooth surface. Additionally, the four-sided tileable sensor stacks allow the sensor stacks to be arranged such that there are no offsets at the boundaries of these tiled sensor stacks, thereby circumventing occurrence of imaging artifacts. Also, the four-sided tileable sensor stacks provide the ability to tile fine pitch sensor stacks into a large area detector without significant offsets between sensor stack edges.

Moreover, use of the interposer circumvents the need for an exact match between the ASIC pad array and the sensor pad array, thereby maintaining a high pitch of the interconnect. In addition, the interposer covers only part of the ASIC area and raises the sensor away from the ASIC surface. These partial coverage and spacing away features create a gap in the tiled detector array structure where wire bonds or other flexible interconnect can be disposed to attach the ASIC bond surface to system electronics. Consequently, the interconnect needs are met while still providing four-sided tileability with fine pitch sensor.

Also, a flat panel detector may be constructed from an array of sensor stacks with sensor elements all in the same plane. Furthermore, a CT arc detector array may also be constructed by tiling these sensor stacks, where although the modules are not in the same plane globally, the edges of the modules lined up without offsets. The sensor stacks allow creation of different geometries of detector arrays while maintaining a small pitch sensor. Additionally, the sensor stacks provide a means to electrically connect one side of the ASIC to the sensor and also facilitate coupling the same side of the ASIC to the system electronics.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for forming a sensor stack, comprising:
   providing a substrate having a first side and a second side;
   disposing an integrated circuit having a first side and a second side on the first side of the substrate, wherein the integrated circuit comprises a first plurality of contact pads disposed on the first side of the integrated circuit;
   providing a sensor array having a plurality of sensor elements, wherein each of the sensor elements has a first side and a second side, and wherein the sensor array comprises a second plurality of contact pads disposed on a second side of the sensor array;
   disposing an interposer having one or more interposer elements and one or more through vias disposed therethrough between the one or more sensor elements of the sensor array and the integrated circuit to raise the sensor array away from the first side of the integrated circuit such that a plane of the one or more sensor elements is locally normal to a sensor stack normal, wherein the interposer is configured to couple the second side of the sensor elements in the sensor array to the first side of the integrated circuit; and
   operationally coupling the first plurality of contact pads on the first side of the integrated circuit to the second plurality of contact pads on the second side of the sensor array to form a tileable sensor stack.

2. The method of claim 1, wherein the sensor array comprises a computed tomography detector array, an X-ray detector array, an ultrasound transducer array, or combinations thereof.

3. The method of claim 1, wherein the one or more interposer elements in the interposer have an angled profile.

4. The method of claim 3, wherein the one or more interposer elements in the interposer have a rectangular shape, a wedge shape, a square shape, a circular shape, or combinations thereof.

5. The method of claim 1, wherein the one or more interposer elements in the interposer have a varying thickness.

6. The method of claim 1, wherein the interposer further comprises one or more routing layers.

7. The method of claim 1, further comprising disposing the one or more sensor elements in the sensor array over a portion of an area of the integrated circuit.

8. The method of claim 1, further comprising disposing a spacer element between the second side of the integrated circuit and the substrate.

9. The method of claim 1, further comprising operationally coupling the integrated circuit to other electronics using wire bonds or flexible interconnect.

10. The method of claim 9, wherein operationally coupling the integrated circuit to the other electronics comprises disposing the wire bonds or the flexible interconnect in a clearance space created between the sensor array and the integrated circuit.

11. A method for forming a tileable detector array, comprising:
    forming a tileable sensor stack, comprising:
       providing a sensor element having a first side and a second side, wherein the sensor element comprises a first plurality of contact pads disposed on the second side of the sensor element;
       disposing the sensor element on a portion of an area of an integrated circuit having a first side and a second side;
       disposing a wedge shaped interposer element between the sensor element and the integrated circuit, wherein the wedge shaped interposer element is configured to raise the sensor element away from the first side of the integrated circuit such that a plane of the sensor element is locally normal to a sensor stack normal, wherein the wedge shaped interposer element comprises through vias disposed therethrough, and wherein the interposer is configured to operationally couple the second side of the sensor element to the first side of the integrated circuit;
       operationally coupling the first plurality of contact pads on the second side of the sensor element to a second plurality of contact pads on the first side of the integrated circuit to form the tileable sensor stack; and
    tiling a plurality of tileable sensor stacks on a first side of a substrate to form the tileable detector array.

12. The method of claim 11, further comprising disposing a spacer element between the second side of the integrated circuit and the first side of the substrate, wherein the spacer element is configured to compensate for the wedge shape of the interposer element.

13. The method of claim 11, further comprising operationally coupling the integrated circuit to other electronics using wire bonds or flexible interconnect.

14. The method of claim 13, wherein operationally coupling the integrated circuit to the other electronics comprises disposing the wire bonds or the flexible interconnect in a clearance space created between the sensor element and the integrated circuit.

15. A method for forming a tileable detector array, comprising:
    forming a first plurality of tileable stepped sensor stacks, comprising:

providing a sensor element having a first side and a second side, wherein the sensor element comprises a first plurality of contact pads disposed on the second side of the sensor element;

disposing the sensor element on a portion of an area of an integrated circuit having a first side and a second side;

disposing an stepped interposer element between the sensor element and the integrated circuit, wherein the stepped interposer element is configured to raise the sensor element away from the first side of the integrated circuit such that a plane of the sensor element is locally normal to a sensor stack normal, wherein the stepped interposer element comprises through vias disposed therethrough, and wherein the stepped interposer element is configured to operationally couple the second side of the sensor element to the first side of the integrated circuit;

operationally coupling the first plurality of contact pads on the second side of the sensor element to a second plurality of contact pads on the first side of the integrated circuit to form the first plurality of tileable stepped sensor stacks;

forming a second plurality of sensor stacks, comprising:
providing a sensor element having a first side and a second side, wherein the sensor element comprises a first plurality of contact pads disposed on the second side of the sensor element;
disposing the sensor element on a portion of an area of an integrated circuit having a first side and a second side;
operationally coupling the first plurality of contact pads on the second side of the sensor element to a second plurality of contact pads on the first side of the integrated circuit to form the second plurality of tileable stepped sensor stacks; and tiling the first plurality of tileable stepped sensor stacks and the second plurality of sensor stacks on a first side of a substrate to form the tileable detector array.

16. The method of claim 15, wherein disposing the stepped interposer element between the sensor element and the integrated circuit comprises using a stepped interposer element having different thicknesses.

17. The method of claim 15, further comprising operationally coupling the integrated circuit to other electronics using wire bonds or flexible interconnect.

18. The method of claim 17, wherein operationally coupling the integrated circuit to the other electronics comprises disposing the wire bonds or the flexible interconnect in a clearance space created between the sensor element and the integrated circuit.

19. The method of claim 15, further comprising disposing a spacer element between the second side of the integrated circuit and the first side of the substrate.

20. A detector array, comprising:
a substrate having a first side and a second side;
a plurality of tileable sensor stacks arranged on the first side of the substrate to form a planar detector array, wherein each of the plurality of tileable sensor stacks comprises:
a sensor element having a first side and a second side, wherein the sensor element comprises a first plurality of contact pads disposed on the second side of the sensor element;
an integrated circuit having a first side and a second side;
an interposer element having one or more through vias disposed therethrough, wherein the interposer element is disposed between the sensor element and the integrated circuit and configured to raise the sensor array away from the first side of the integrated circuit such that a plane of the sensor element is locally normal to detector array normal, and wherein the interposer element is configured to operationally couple the second side of the sensor element to the first side of the integrated circuit,
wherein the first plurality of contact pads on the second side of the sensor element is operationally coupled to a second plurality of contact pads on the first side of the integrated circuit to form the tileable sensor stack.

21. The detector array of claim 20, wherein the detector array comprises a flat panel detector array, an arc detector array, or a combination thereof.

22. The detector array of claim 20, wherein the interposer element comprises a stepped interposer element or a wedge shaped interposer element.

23. The detector array of claim 22, wherein the stepped interposer element comprises an interposer element having a varying thickness.

24. The detector array of claim 22, wherein the interposer element further comprises one or more routing layers, one or more routing traces, or both the one or more routing layers and the one or more routing traces.

25. The detector array of claim 24, wherein the interposer element further comprises top contact pads disposed on a first side of the interposer element and bottom contact pads disposed on a second side of the interposer element.

26. The detector array of claim 20, wherein the sensor element is disposed over a portion of an area of the integrated circuit.

27. The detector array of claim 20, further comprising a spacer element disposed between the second side of the integrated circuit and the first side of the substrate.

* * * * *